United States Patent
Bayraktar et al.

(10) Patent No.: US 11,899,157 B2
(45) Date of Patent: Feb. 13, 2024

(54) WELL LOGGING TOOL AND INTERPRETATION FRAMEWORK THAT EMPLOYS A SYSTEM OF ARTIFICIAL NEURAL NETWORKS FOR QUANTIFYING MUD AND FORMATION ELECTROMAGNETIC PROPERTIES

(71) Applicant: SCHLUMBERGER TECHNOLOGY CORPORATION, Sugar Land, TX (US)

(72) Inventors: Zikri Bayraktar, Cambridge, MA (US); Dzevat Omeragic, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 276 days.

(21) Appl. No.: 17/288,597

(22) PCT Filed: Oct. 24, 2019

(86) PCT No.: PCT/US2019/057903
§ 371 (c)(1),
(2) Date: Apr. 26, 2021

(87) PCT Pub. No.: WO2020/086874
PCT Pub. Date: Apr. 30, 2020

(65) Prior Publication Data
US 2021/0396903 A1 Dec. 23, 2021

Related U.S. Application Data

(60) Provisional application No. 62/751,083, filed on Oct. 26, 2018.

(51) Int. Cl.
*G01V 3/24* (2006.01)
*G01N 33/28* (2006.01)
*G01V 3/38* (2006.01)

(52) U.S. Cl.
CPC .......... *G01V 3/24* (2013.01); *G01N 33/2823* (2013.01); *G01V 3/38* (2013.01)

(58) Field of Classification Search
None
See application file for complete search history.

(56) References Cited

U.S. PATENT DOCUMENTS 7,066,282 B2  6/2006  Chen et al.
7,241,194 B2  7/2007  Tawa et al.
(Continued)

FOREIGN PATENT DOCUMENTS

WO  02093126 A2  11/2002

OTHER PUBLICATIONS

International Preliminary Report on Patentability of International Patent Application No. PCT/US2019/057903 dated May 6, 2021, 7 pages.
(Continued)

*Primary Examiner* — Lina Cordero
(74) *Attorney, Agent, or Firm* — Ashley E. Brown

(57) ABSTRACT

Methods and systems are provided that predict electromagnetic properties of drilling mud and a formation, which involve a logging tool that measures current injected into a measurement zone adjacent a sensor electrode at multiple frequencies. The measured currents at the multiple frequencies are processed to determine complex impedances for the sensor electrode at the multiple frequencies. The complex impedances are used to generate input data, which is supplied to a system of artificial neural networks (ANNs) that is configured to predict and output electromagnetic proper-
(Continued)

ties of the drilling mud and the formation within the measurement zone and possibly tool standoff based on the input data. The system of ANNs can employ a cascaded architecture of multiple ANNs. The electromagnetic properties or tool standoff predicted by the system of ANNs can be used to construct a borehole image over varying azimuth and depth.

21 Claims, 12 Drawing Sheets

(56) References Cited

U.S. PATENT DOCUMENTS

| | | |
|---|---|---|
| 7,265,553 B2 | 9/2007 | Cheung et al. |
| 8,754,651 B2 | 6/2014 | Habashy et al. |
| 8,776,878 B2 | 7/2014 | Bloemenkamp et al. |
| 9,400,339 B2 | 7/2016 | Bloemenkamp et al. |
| 9,513,399 B2 | 12/2016 | Cheung et al. |
| 9,678,239 B2 | 6/2017 | Habashy et al. |
| 2005/0067190 A1 | 3/2005 | Tabanou et al. |
| 2006/0265150 A1* | 11/2006 | Hu ................ G01N 33/2823 702/50 |
| 2009/0030858 A1 | 1/2009 | Hegeman et al. |
| 2010/0211536 A1 | 8/2010 | Al-Fattah |
| 2012/0209527 A1 | 8/2012 | Gorek et al. |
| 2013/0119994 A1* | 5/2013 | Csutak ................ G01V 3/30 324/338 |
| 2020/0041395 A1* | 2/2020 | Swett ................ G01N 9/002 |

OTHER PUBLICATIONS

Bloemenkamp et al., "Design and field testing of a new high-definition microresistivity imaging tool engineered for oil-based mud," Transactions of the 55th Annual SPWLA Logging Symposium, Abu Dhabi, May 18-22, 2014.

Chen et al., "Inversion-based workflow for quantitative interpretation of the new-generation oil-based mud resistivity imager," Transactions of the 55th Annual SPWLA Logging Symposium, Abu Dhabi, May 18-22, 2014.

Search Report and Written Opinion of International Patent Application No. PCT/US2019/057903 dated Feb. 10, 2020; 10 pages.

\* cited by examiner

WELL LOGGING TOOL AND INTERPRETATION FRAMEWORK THAT EMPLOYS A SYSTEM OF ARTIFICIAL NEURAL NETWORKS FOR QUANTIFYING MUD AND FORMATION ELECTROMAGNETIC PROPERTIES

CROSS-REFERENCE TO RELATED APPLICATION(S)

The subject disclosure claims priority from U.S. Provisional App. No. 62/751,083, filed on Oct. 26, 2018, entitled "ARTIFICIAL NEURAL NETWORK BASED QUANTITATIVE INTERPRETATION METHOD OF OIL-BASE MUD RESISTIVITY IMAGER", herein incorporated by reference in its entirety.

FIELD

The subject disclosure relates to well logging tools and interpretation frameworks that quantify mud and formation electromagnetic properties.

BACKGROUND

Electromagnetic (EM) well-logging tools are one of the many classes of well-logging tools (others include Gamma Ray (GR) tools and Nuclear Magnetic Resonance Imaging (NMRI) tools) used for oilfield applications. EM logging tools have been a subject of interest for many decades due to their capability to measure the conductivity (or resistivity) of an earth formation. The basic concept can be explained by a simple tool which consists of single transmitter coil and single receiver coil inside a borehole. The transmitter coil excites an alternating current (ac) inducing an alternating EM field that propagates/diffuses through the earth formation. This EM field induces an electric current on the receiver coil. The electric current induced on the receiver is proportional to the conductivity of the formation. Hence, the resistivity of the formation can be estimated. If the porosity of the earth is also known, well-logging analysts can use the Archie equation as a guideline to determine the saturation of oil within the formation surrounding the EM logging tool.

In practice, EM logging tools can operate thousands of feet underneath the earth surface in a complex environment where detailed formation properties are unknown. The measured conductivity represents an average effective conductivity of the earth formation in the vicinity of the EM logging tool. The formation itself can exhibit inhomogeneities such as layered beds, dipping beds, anisotropy, and invaded zones by drilling fluid. Moreover, the EM logging tool may be misaligned with the borehole (eccentric tool) due to gravitational pull or mechanical vibration. In order to perform accurate formation evaluation, modeling and analysis of the response of the EM logging tool in complex formations is essential.

Before the advent of high-performance computing, costly experiment or approximate analytical techniques were the only option to study EM tool response. With the advance of computing capabilities, well-logging analysts have turned to computer modeling as the most cost-effective way to understand the tool response in complex formations.

Well-logging and formation evaluation refer to the process of acquiring and interpreting information of the earth formation properties (including resistivity and porosity) as a function of depth and azimuth of a borehole. The term "formation" in the formation evaluation context means the earth media surrounding the borehole. Earth formations usually include horizontal layers each having different properties and varying thickness. Earth media can be categorized by their electrical properties (permittivity, conductivity), which can often (but not always) be assumed uniform within a layer. The variation on the tool response as the tool crosses layer interfaces is known as shoulder-bed effects.

The formation conductivity can exhibit anisotropy, which can be due to fractured formations that when filled with saltwater or brine displays a higher conductivity in the direction parallel to the fracture plane than in the perpendicular direction or it can be due to sand/clay laminae with differential electrical properties that can be treated as macro-anisotropy.

In order to minimize the operational cost and environmental impact, directional drilling has become increasingly prevalent in recent years. By using directional drilling, the drill bit is geo-steered such that a borehole traverses the oil zone of the formation. During directional drilling, the layer becomes dipped with respect to the well-logging tool axis. Moreover, during directional drilling, due to the gravitational pull on the tool and mechanical vibration, the tool axis can be displaced inside the borehole. The degree of off-center between the tool axis and the borehole axis is denoted as tool eccentricity. The shortest distance between the external sensor of the tool and the borehole wall is denoted as standoff. The standoff can vary over azimuthal direction due to tool eccentricity and borehole surface rugosity. The eccentric effect or variations in standoff can become significant if the borehole is large with respect to the diameter of the tool itself.

In the process of drilling, the drilling fluid that fills the borehole is called mud. The mud can be either water-based (high conductivity) or oil-based (low conductivity) and can infiltrate into formation depending on the porosity and the differential pressure. In this case, an invasion zone is formed which includes the mud infiltrate in the pore space of the formation rock. This invasion zone acts as a transition region between the borehole mud and the actual formation. The invasion zone exhibits electric properties that are different from the borehole mud and the actual formation.

The currently available technology for EM well logging employs an inversion-based workflow that characterizes formation resistivity and formation permittivity in a manner that accounts for standoff. Such inversion-based workflows can be used for boreholes drilled with either water-based mud or oil-based mud. Such inversion-based workflows can be integrated as part of a wireline logging tool where the logging is carried out in a borehole after the drilling operation of the borehole is completed. Alternatively, such inversion-based workflows can be integrated as part of a measurement-while-drilling (MWD) or logging-while-drilling (LWD) tool, where the logging measurements and drilling of the borehole are performed simultaneously.

In general, the inversion-based workflows have essentially two parts. The first part is a forward model that generates a synthetic log from a synthetic test formation which is a representation of a real formation (including EM properties of the formation and mud as well as standoff). The forward model simulates the response of the EM logging tool to the synthetic test formation to generate the synthetic log. The second part involves modifying or updating the EM properties of the test formation and/or standoff based on the difference between the synthetic log corresponding to the test formation and the real log data measured by the EM logging tool. After the EM properties of the test formation and/or standoff have been modified, a new synthetic log is generated by the forward model. This process is repeated iteratively until the difference between the synthetic log and the real log satisfies a predefined stopping criterion. The output of the inversion-based workflow is the EM properties (resistivity) of the formation and mud as well as standoff as part of the final test formation. These properties can be plotted as a function of depth to produce the desired log. The iterative nature of these workflows makes them computationally intensive, relatively slow and prone to poor convergence in unfavorable conditions for large standoff and high formation resistivities.

SUMMARY

This summary is provided to introduce a collection of concepts that are further described below in the detailed description. This summary is not intended to identify key or essential features of the claimed subject matter, nor is it intended to be used as an aid in limiting the scope of the claimed subject matter.

In accordance with the subject disclosure, methods and systems are provided that predict electromagnetic properties of drilling mud and formation, which involve a logging tool that measures current injected into a measurement zone adjacent a sensor electrode at multiple frequencies. The measured currents at the multiple frequencies are processed to determine complex impedances for the sensor electrode at the multiple frequencies. The complex impedances are used to generate input data, which is supplied to a system of artificial neural networks (ANNs) that is configured to predict and output electromagnetic properties of the drilling mud and the formation within the measurement zone and possibly tool standoff based on the input data. The system of ANNs can employ a cascaded architecture of multiple ANNs. The electromagnetic properties or tool standoff predicted by the system of ANNs can be used to construct a borehole image over varying azimuth and depth.

This new approach eliminates the need for iterative inversion. Instead, the system of ANNs is trained and used as nonlinear regressors to predict the mud and formation parameters as well as the tool standoff for each sensor electrode separately. Using the individual sensor measurements, the system of ANNs can operate at an order of magnitude faster speed than the inversion.

In embodiments, the system of ANNs can employ a cascaded architecture of multiple ANNs, where one or more mud or formation parameters determined by an ANN are passed on as inputs to another ANN in the cascaded architecture. The methodology also allows for easier integration with other measurements and training the neural networks on field data, targeting specific scenarios and range of parameters for formations or areas.

BRIEF DESCRIPTION OF DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Figure 1:
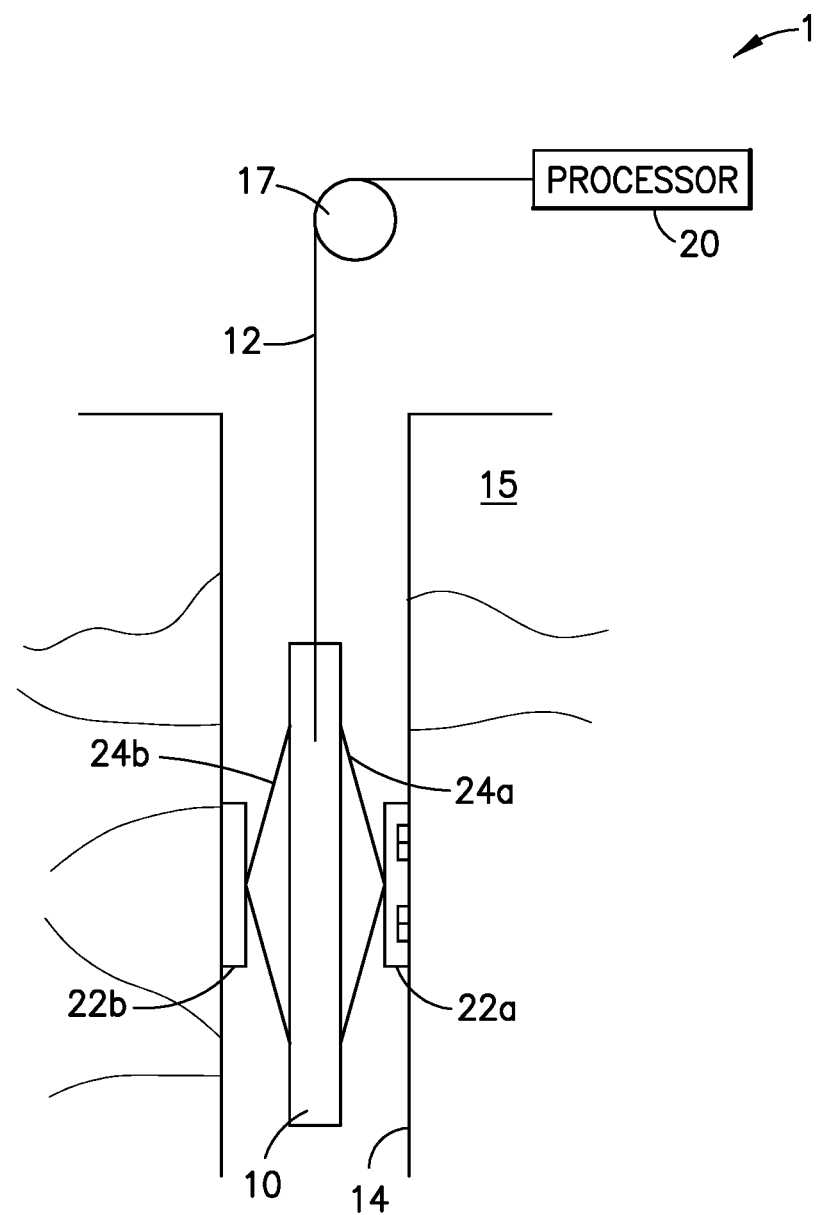
FIG. 1 is a block diagram of a well logging system that can incorporate aspects of the subject disclosure.

Turning now to FIG. 1, a wireline logging system 1 that can embody aspects of the present disclosure includes a tool 10 which is suspended via a cable 12 in a borehole 14 which traverses a formation 15. The cable 12 is wound about a winch 17 or suitable suspension means located at the surface of the earth formation, and may be utilized, if desired, to carry information which is sent by the tool 10 to a processor 20. The tool 10 is shown with pads (two shown as 22a, 22b) which are pressed against mudcake (not shown) on the borehole wall using spring arms 24a, 24b. In accordance with embodiments, information is gathered by the tool 10 by use of one or more electrodes located on the pads 22a, 22b.

As is well known in the art, the gathered information may be preprocessed downhole by a processor (not shown) associated with the tool 10 and may be sent via the cable 12, or via wireless mechanisms (e.g., mud pulsing) to the surface-located processor 20 for additional processing. The processor 20 may be located in the vicinity of the formation 15 or at another site as desired. Alternatively, raw data may be sent to the processor 20. As has been previously established, the mudcake on the borehole wall may be relatively conductive in the case where water-based mud is used in the borehole or may be relatively resistive in the case where oil-base mud is used in the borehole. It is desirable that the tool 10 can be configured for use in both situations. In other embodiments, the logging tool 10 can be a measurement-while-drilling logging tool that is part of a measurement-while-drilling system that includes a bottom-hole assembly with a drill bit that is operated to drill the borehole that traverses the formation.

Figure 2:
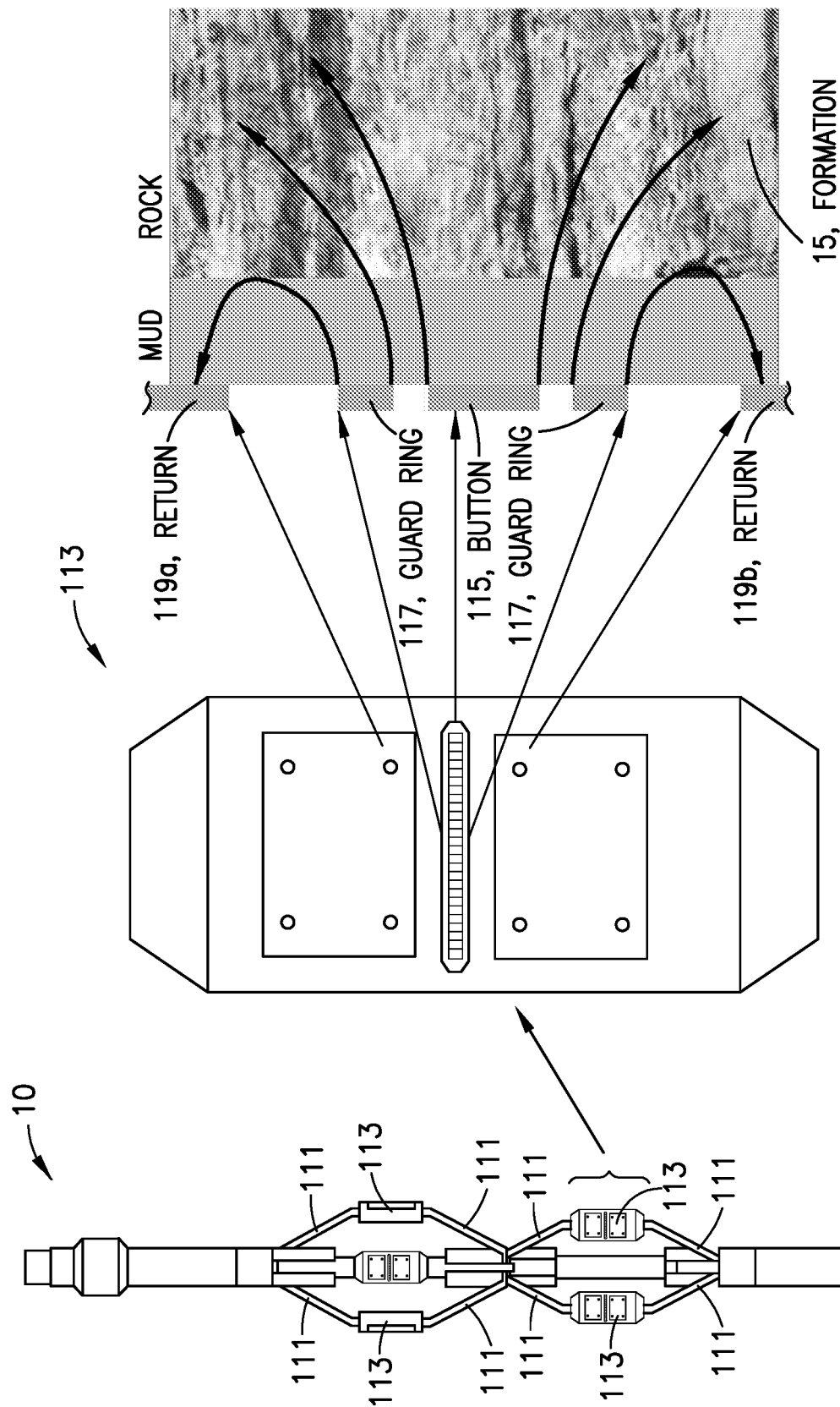
FIG. 2 is a schematic illustration of the logging tool of FIG. 1 and its operation in the borehole environment.

As shown in FIG. 2, the logging tool 10 can include eight (8) double arms 111 that are equipped with eight (8) pads 113. The arms 111 can be independently actuated such that the respective pads 113 can be placed in close contact with the borehole wall under borehole conditions. The double arms 111 can employ spring forces that allow for the pads 113 to carry out electromagnetic measurements during movement (such as descent) of the tool 10, while minimizing stick-and-slip effect on quality of the electromagnetic measurements. In embodiments, the arms 111 and pads 113 can be configured to allow a given pad to swivel up to 15 degrees around the long axis of the arm that supports it and change pitch angle of the given pad. These features allow the pads to maintain reliable contact with the borehole wall, even in highly deviated wells and pore borehole conditions. Each pad 113 includes an array of microelectrodes or buttons 115 (such as an array of 24 buttons) that are surrounded by a guard ring 117. Each button 115 can have a surface area of approximately 11 mm$^2$ or less. The guard ring 117 is located between two larger return electrodes 119A, 119B. The buttons 115 and the guard ring 117 are kept at the same electric potential and operate as current injectors. The two return electrodes 119A, 119B are kept at the same electric potential. The buttons 115 are configured as injectors that apply a high frequency alternating-current (AC) voltage between the current injector, including respective buttons 115 and guard rings 117, and the return electrodes 119A, 119B, which causes current to flow out from each button 115 into a measurement zone that includes drilling mud and the formation disposed adjacent the button 115. The drilling mud in the measurement zone can be mudcake deposited on the borehole wall during drilling and/or mud filtrate that is forced into the pore space of the reservoir rock during drilling. The current flows into the drilling mud and into formation of the measurement zone and then back to the return electrodes 119A, 119B as shown. In embodiments, the respective buttons 115 can be configured to apply AC voltage at two high frequencies F1, F2 in the megahertz range, which reduces the effect of nonconductive (oil-based) mud on the measurement. These sensors are described in co-owned U.S. Pat. Nos. 7,066,282 and 8,754,651, which are herein incorporated by reference in their entireties.

In the subject disclosure, the logging system employs an arrangement of artificial neural networks (ANNs) that are configured and trained to predict mud and formation electromagnetic properties as well as standoff for each button directly from the sensor measurements without using inversion or electromagnetic forward modeling, providing an order of magnitude speed up in prediction. An artificial neural network (ANN) is a computational system that is inspired by, but not identical to biological neural networks that constitute animal brains. Such systems are trained (or "learn") to perform specific tasks by considering examples. For example, in image recognition, an ANN might learn to identify images containing cats using example images that have been manually labeled as "cat" or "no cat". The resulting trained ANN can then be used to identify other images containing cats. It can do this without any prior knowledge of cats, for example, that they have fur, whiskers and cat-like faces.

An ANN employs a collection of connected units or nodes called artificial neurons, which loosely model the neurons in a biological brain. Each connection, like the synapses in a biological brain, can transmit a signal to other artificial neurons. An artificial neuron that receives a signal can process it and signal one or more artificial neurons connected to it. In an ANN, the signal at a connection is a real number or integer, and the output of each artificial neuron is computed by some non-linear function of the sum of its inputs. The connections are called edges. The edges typically have weights that increase or decrease the strength of the respective signals for the connections. The weights are adjusted as learning proceeds. Artificial neurons can have a threshold such that a signal is sent only when the signal crosses the threshold.

Typically, the artificial neurons of the ANN are organized as layers that each includes one or more artificial neurons, where the layers include an input layer (first layer), an output layer (last layer) and one or more hidden layers between the input layer and the output layer. The input layer receives external data. The output layer produces result data. In a feedforward neural network, the connections between the artificial neurons do not form a cycle. The information moves in only one direction, forward, from the input layer to the hidden layer(s), if any, and to the output layer. There are no cycle or loops in the network. In this case, the artificial neurons of a given hidden layer can connect to artificial neurons of the immediately preceding and immediately following layers.

The ANN has hyperparameters, which are inherent parameters whose values are set before the learning process begins. Typical examples of hyperparameters include learning rate, the number of layers and number of neurons per layer. The learning process is the adaptation of the ANN to better handle a task by considering labeled observations as inputs to the ANN. The learning process typically involves adjusting the weights (and possibly thresholds) of the ANN to improve the accuracy of the result data. This is typically accomplished by minimizing a cost function that represents a measure of the accuracy of the result data of the ANN with respect to a given labeled observation as input. The learning rate typically defines the size of the corrective step that the ANN will take in adjusting the weights (and possibly thresholds) of the ANN.

The learning process of the ANN can employ supervised learning. In supervised learning, the learning process uses a set of paired observations and desired outputs or labels, and the learning task is for the ANN to produce the desired output or label for the paired observation taken as input to the ANN. In this case, the cost function is related to eliminating incorrect deductions. A commonly used cost is the mean-squared error, which tries to minimize the average squared error between the output of the ANN and the desired output or label.

Figure 3A:
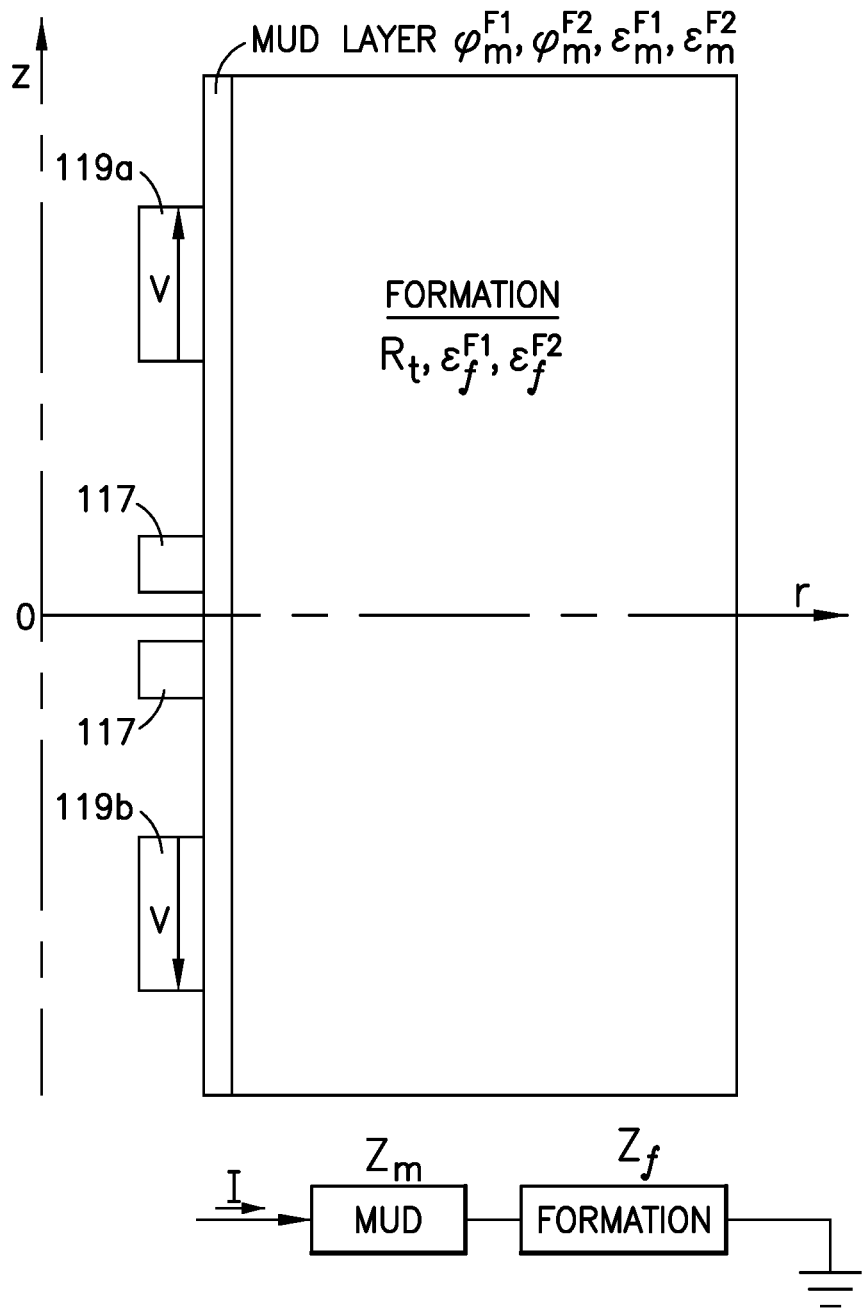
FIGS. 3A, 3B and 3C are diagrams that depict a model parameterization that is useful in understanding the theoretical relationships of the formation and drilling mud parameters that can be predicted from individual sensor measurements made in the borehole environment.
Figure 3C:
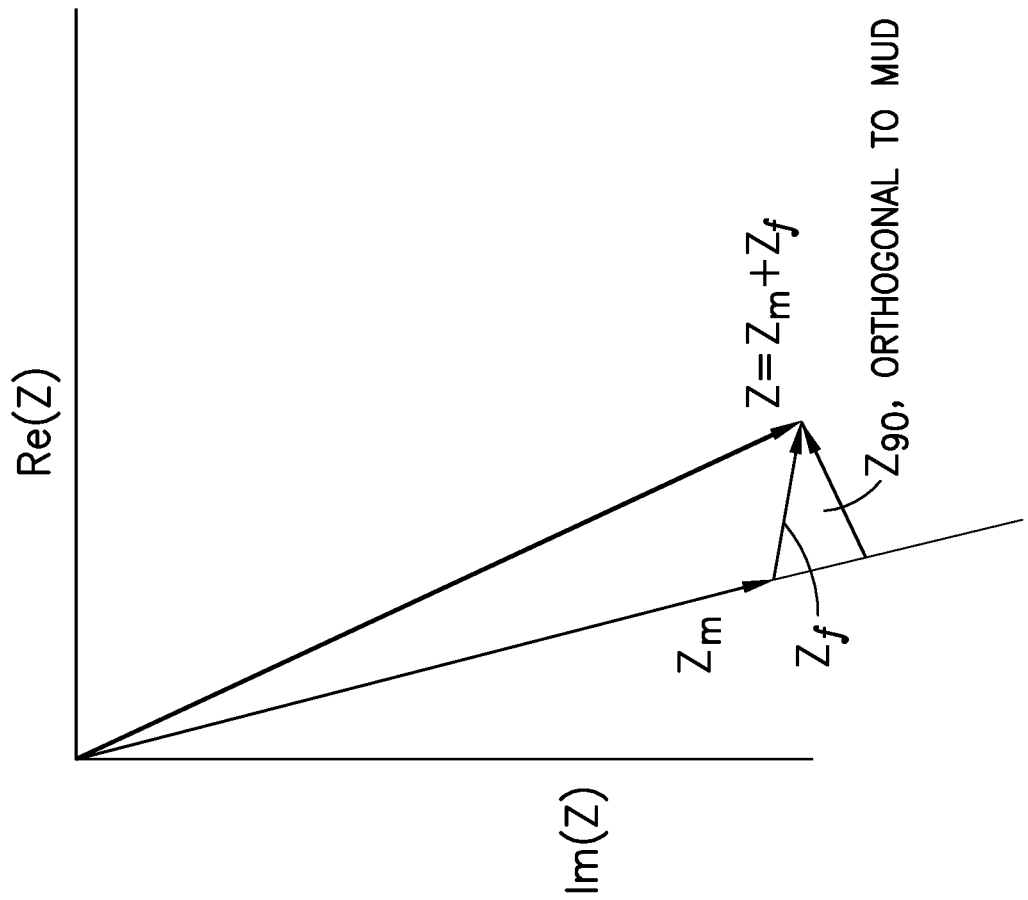
Figure 3B:
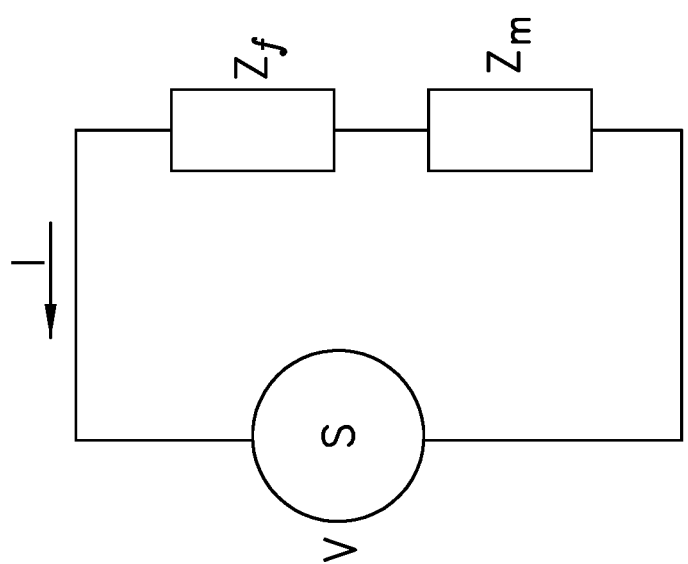

In embodiments, the prediction of mud and formation electromagnetic properties as well as tool standoff for each button is intrinsically an under-determined problem, where more unknowns need to be determined than available measured values. For example, the mud and formation electromagnetic properties for each button can be parameterized by a model shown in FIGS. 3A, 3B and 3C, which has eight parameters that include formation resistivity $R_t$, formation permittivity at two frequencies F1, F2 in the megahertz range given as $\varepsilon_f^{F1}$ and $\varepsilon_f^{F2}$, mud impedance angles at the two frequencies F1, F2 given as $\varphi_m^{F1}$ and $\varphi_m^{F1}$, mud permittivity at the two frequencies F1, F2 given as $\varepsilon_m^{F1}$ and $\varepsilon_m^{F2}$, and tool standoff S for a given button. These eight parameters for a given button can be predicted by the arrangement of artificial neural networks (ANNs) from the measured impedances (two complex values) of the given button at the two frequencies F1, F2. The complex value button impedance is modeled as a series combination of the complex formation impedance $Z_f$ and the complex mud impedance $Z_m$ as shown in FIG. 3B or as phasor diagram on FIG. 3C. In cases, where the formation impedance $Z_f$ is small, $Z_{90}$ can project the formation impedance $Z_f$ to the direction orthogonal to the mud impedance $Z_m$ as shown in the phasor diagram of FIG. 3C. The mud impedance angles $\varphi_m^{F1}$ and $\varphi_m^{F1}$ are the phase angle of the complex mud impedance $Z_m$ at the two frequencies F1, F2. The formation resistivity $R_t$ can be equated to the real part of the complex formation impedance $Z_f$. Note that other suitable parameterization models can also be used.

Figure 4:
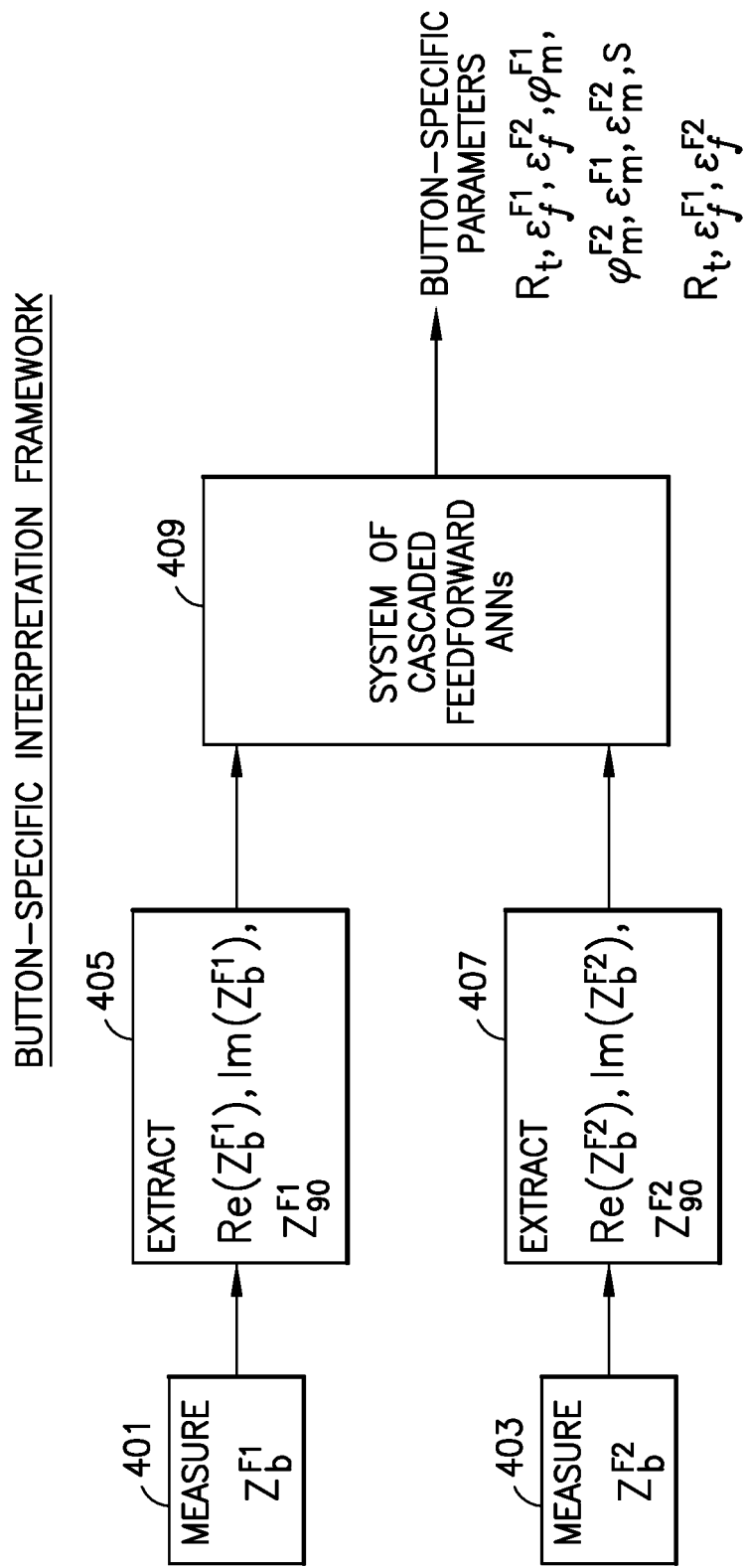
FIG. 4 is a block diagram of an interpretation framework that predicts formation and drilling mud parameters as well as tool standoff for a sensor of a logging tool from measurements made by the sensor in the borehole environment.

FIG. 4 is a block diagram of an interpretation framework that can be embodied as part of the logging system. The framework can be used for applications where the borehole is drilled with oil-based mud. The framework includes block 401 where the logging tool 10 is configured to apply an alternating voltage of frequency F1 to one or more button electrodes 115 such that button electrode(s) injects current into a measurement zone disposed adjacent the respective button electrode(s). The measurement zone for a button includes drilling mud and the formation adjacent the button. The logging tool 10 is also configured to measure the current injected by a button at the frequency and process the measured current to determine a complex valued button impedance $Z_b^{F1}$ as $Z_b^{F1}=V_r/I_b$ at F1. In block 403, the logging tool 10 is configured to apply an alternating voltage of frequency F2 to a one or more button electrodes 115 such that button electrode(s) inject current into the same measurement zone disposed adjacent the respective button electrode(s) of block 401. The logging tool 10 is also configured to measure the current injected by the button at frequency F2 and process the measured current to determine a complex valued button impedance $Z_b^{F2}$ as $Z_b^{F2}=V_r/I_b$ at F2. The details of these current and impedance measurements can be found in, Bloemenkamp et al., "Design and field testing of a new high-definition microresistivity imaging tool engineered for oil-based mud", 55th annual SPWLA conference, Abu Dhabi, 2014, hereinafter Bloemenkamp.

In block 405, the complex valued button impedance $Z_b^{F1}$ measured in block 401 is processed to extract the real part ($\text{Re}(Z_b^{F1})$) and the imaginary part ($\text{Im}(Z_b^{F1})$) of the complex valued button impedance $Z_b^{F1}$ as well as an orthogonal impedance component ($Z_{90}^{F1}$). The orthogonal impedance component ($Z_{90}^{F1}$) is a simple approximation for the formation impedance vector that can be computed from the measured impedance at the frequency F1 by projecting the measured impedance at F1 into the direction perpendicular to mud impedivity phasor. For example, the orthogonal impedance component $Z_{90}^{F1}$ can be calculated as: $Z_{90}^{F1}=|Z_b^{F1}|\cdot\sin(\varphi_{Zb}^{F1}-\varphi_m^{F1})$, where $\varphi_m^{F1}$ is the mud angle at F1 and $\varphi_{Zb}^{F1}$ is the phase of the complex button impedance $Z_b^{F1}$ at F1. The mud impedivity can be measured using a separate sensor or the mud angle can be determined using a separate algorithm as described in Bloemenkamp.

In block 407, the complex valued button impedance $Z_b^{F2}$ measured in block 403 is processed to extract the real part ($\text{Re}(Z_b^{F2})$) and the imaginary part ($\text{Im}(Z_b^{F2})$) of the complex valued button impedance $Z_b^{F2}$ as well as an orthogonal impedance component ($Z_{90}^{F2}$). The orthogonal impedance component ($Z_{90}^{F2}$) is a simple approximation for the formation impedance vector that can be computed from the measured impedance at the frequency F2 by projecting the measured impedance at the frequency F2 into the direction perpendicular to mud impedivity phasor. For example, the orthogonal impedance $Z_{90}^{F2}$ can be calculated as: $Z_{90}^{F2}=|Z_b^{F2}|\sin(\varphi_{Zb}^{F2}-\varphi_m^{F2})$, where $\varphi_m^{F2}$ is the mud angle at F2 and $Z_b^{F1}$ is the phase of the complex button impedance $Z_b^{F2}$ at F2.

In block 407, the complex valued button impedance $Z_b^{F2}$ measured in block 403 is processed to extract the real part ($\text{Re}(Z_b^{F2})$) and the imaginary part ($\text{Im}(Z_b^{F2})$) of the complex valued button impedance $Z_b^{F2}$ as well as an orthogonal impedance component ($Z_{90}^{F2}$). The orthogonal impedance component ($Z_{90}^{F2}$) is a simple approximation for the formation impedance vector that can be computed from the measured impedance at the frequency F2 by projecting the measured impedance at the frequency F2 into the direction perpendicular to mud impedivity phasor. For example, the orthogonal impedance $Z_{90}^{F2}$ can be calculated as: $Z_{90}^{F2}=|Z_b^{F2}|\cdot\sin(\varphi_{Zb}^{F2}-\varphi_m^{F2})$, where $\varphi_m^{F2}$ is the mud angle at F2 and $\varphi_{Zb}^{F2}$ is the phase of the complex button impedance $Z_b^{F2}$ at F2.

In block 409, the three independent and button-specific measurements ($\text{Re}(Z_b^{F1})$, $\text{Im}(Z_b^{F1})$, and $Z_{90}^{F1}$) produced in block 405 as well as the three independent and button-specific measurements ($\text{Re}(Z_b^{F2})$, $\text{Im}(Z_b^{F2})$, and $Z_{90}^{F2}$) produced in block 407 are used as inputs to a trained system of cascaded feedforward ANNs, which is configured to predict and output a number of parameters that characterize the mud and formation electromagnetic properties as well as tool standoff for a specific button given the set of inputs. For example, the trained system of cascaded feedforward ANNs can predict and output eight parameters given the set of inputs, which include formation resistivity $R_t$, formation permittivity at two frequencies F1, F2 given as $\varepsilon_f^{F1}$ and $\varepsilon_f^{F2}$, mud impedance angles at the two frequencies F1, F2 given as $\varphi_m^{F1}$ and $\varphi_m^{F2}$, mud permittivity at the two frequencies F1, F2 given as $\varepsilon_m^{F1}$ and $\varepsilon_m^{F2}$, and tool standoff S for a button.

The system of cascaded feedforward ANNs employs a cascaded architecture of multiple artificial neural networks where one or more outputs of one or more ANNs is fed as input to one or more other ANNs. Furthermore, the system of cascaded feedforward ANNs operates on the current measurements for a button 115 and is independent of other buttons providing predictions for unknown mud and formation parameters using only measurements collected at that button.

Figure 7:
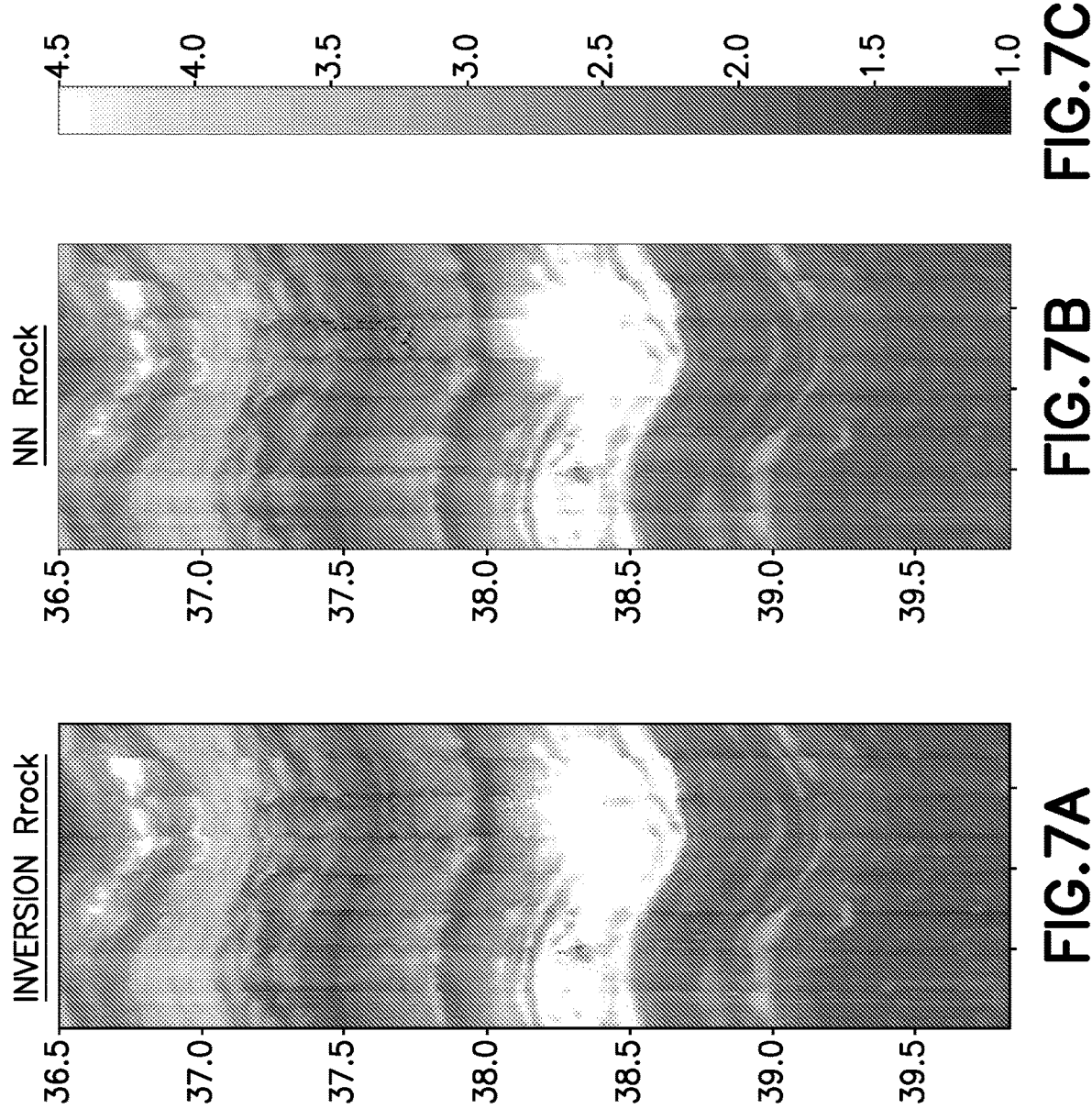
FIGS. 7A, 7B and 7C depict borehole images of formation resistivity produced by inversion processing and the interpretation workflow of FIG. 6 for a data set.
Figure 8:
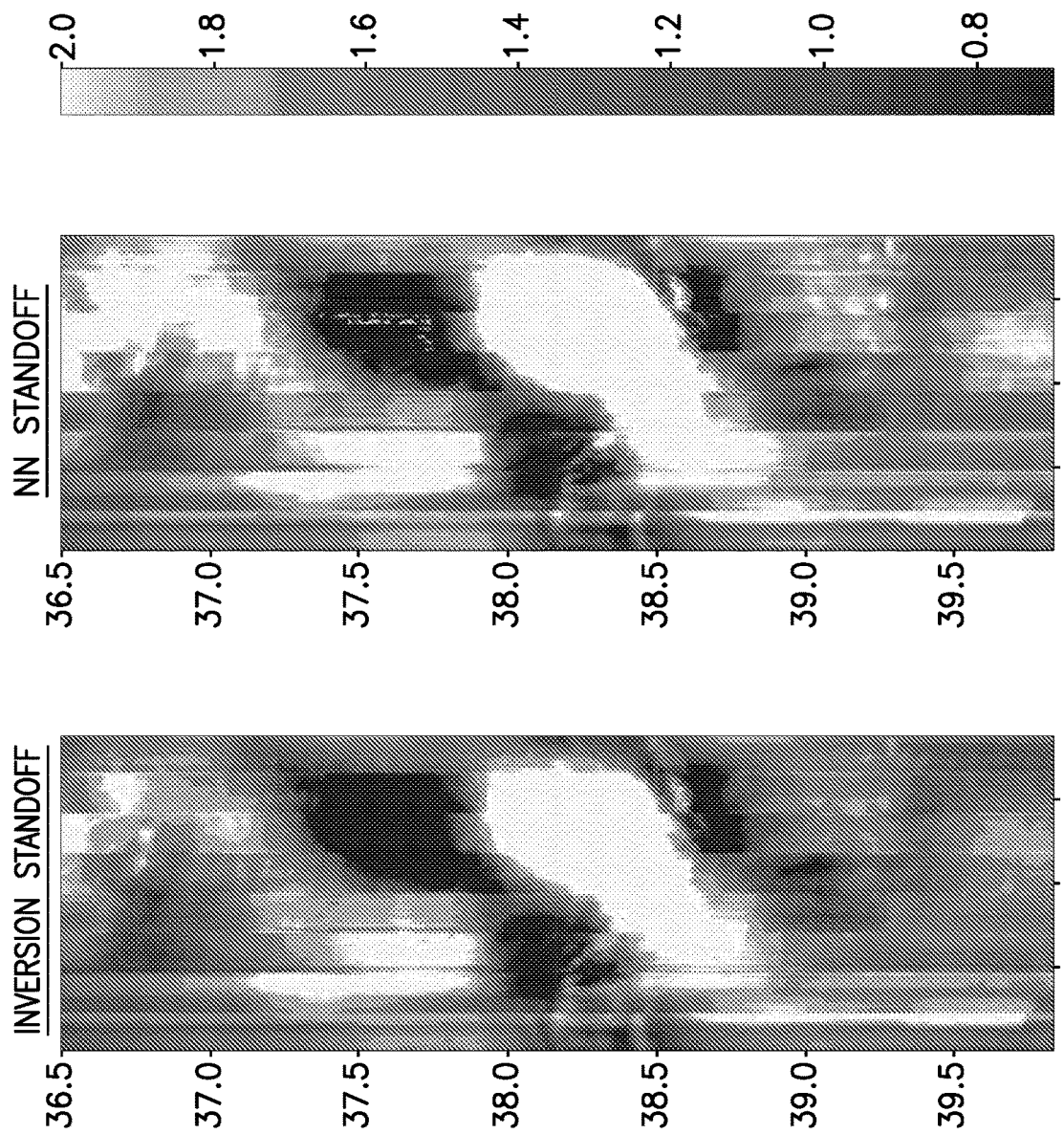
FIGS. 8A, 8B and 8C depict borehole images of tool standoff produced by inversion processing and the interpretation workflow of FIG. 6 for a data set.
Figure 9:
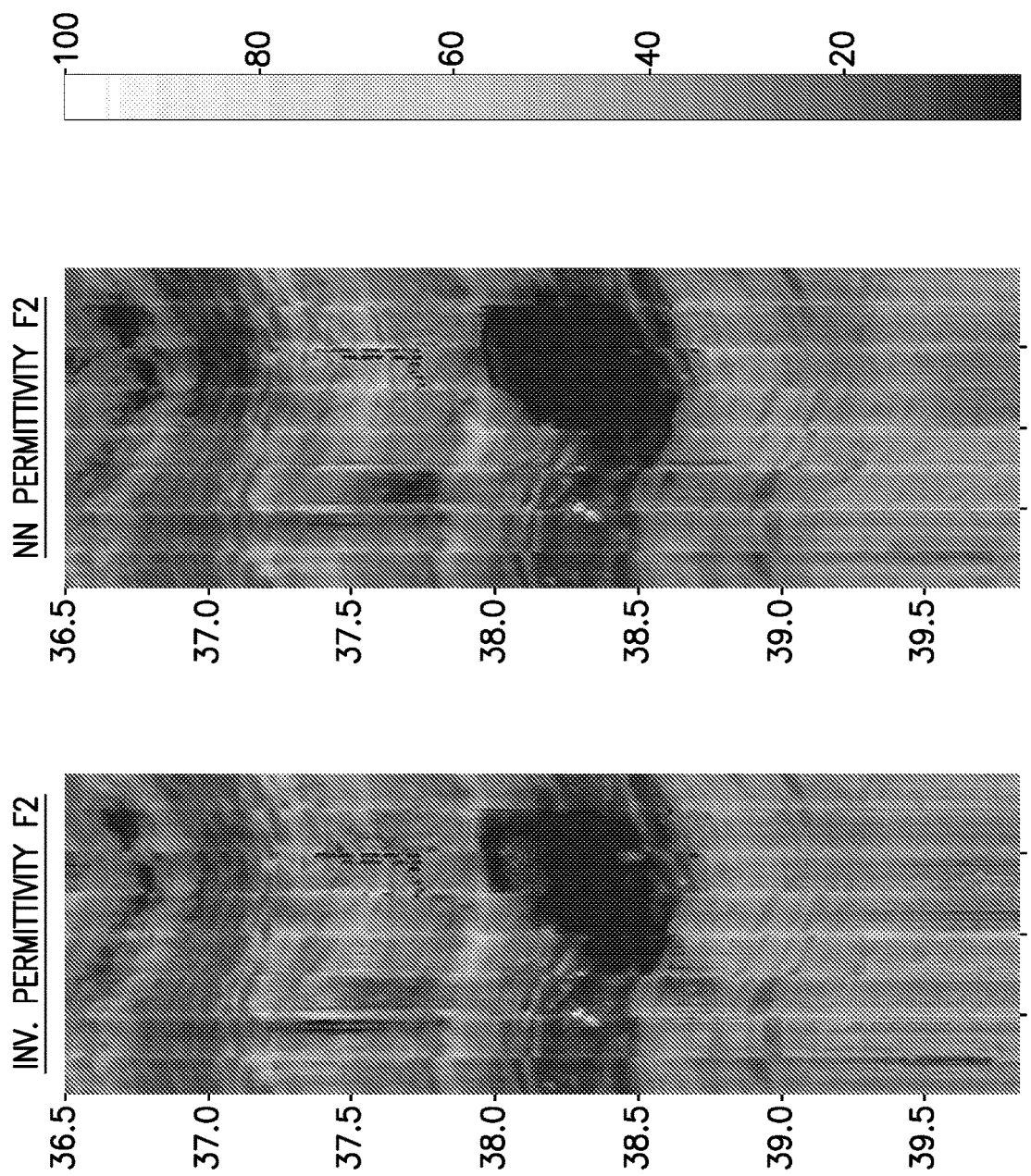
FIGS. 9A, 9B and 9C depict borehole images of formation permittivity produced by inversion processing and the interpretation workflow of FIG. 6 for a data set.

Furthermore, the framework of FIG. 4 can be replicated for every one of the buttons 115 that are part of the same pad 113 and for every one of the buttons of the other pads 113 of the tool. In this configuration, the outputs of the trained system of cascaded feedforward ANNs for the respective buttons can be configured to predict and output mud and formation parameters for the buttons at varying azimuthal coordinates and possibly varying depth coordinates in the borehole. Such parameters can be integrated into one or more images of the borehole or other log. Examples of such images are shown in FIGS. 7B, 8B and 9B below. The image(s) or other log(s) can be displayed or otherwise presented to a user for formation analysis as desired.

Figure 5A:
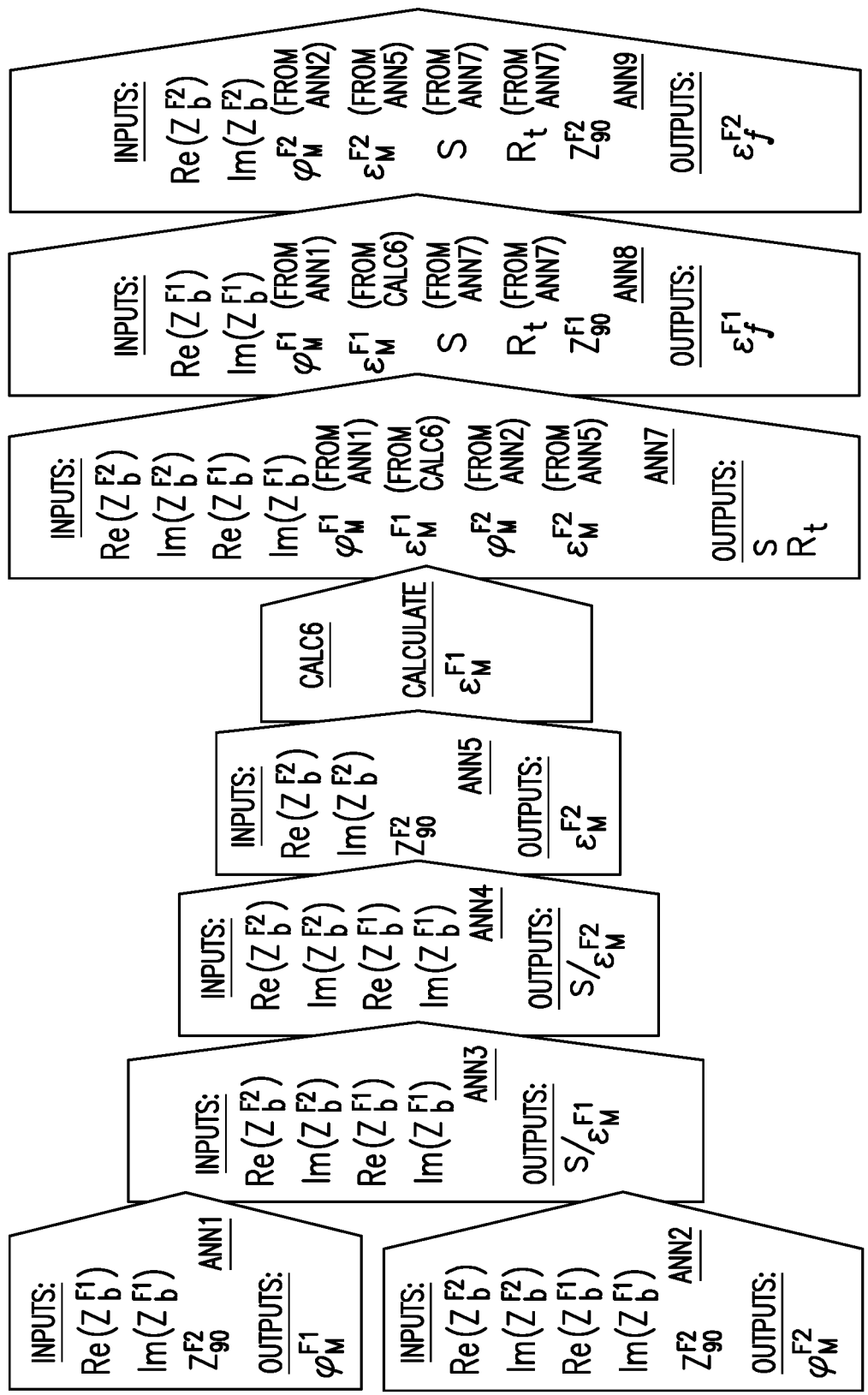
FIG. 5A is a diagram of a system of artificial neural networks (ANNs) which can be used in the framework of FIG. 4; the system employs a cascaded architecture of connected feedforward ANNs with listed inputs and outputs.

In embodiments, the system of cascaded feedforward ANNs can include a number of separate and distinct ANNs that are uniquely trained and combined as shown in FIG. 5A.

ANN1 is an ANN that is configured to take the real and imaginary parts of the button impedance ($\text{Re}(Z_b^{F1})$, $\text{Im}(Z_b^{F1})$) at the frequency F1 and $Z_{90}^{F2}$ as inputs to predict and output the mud impedance angle $\varphi_m^{F1}$ at the frequency F1.

ANN2 is an ANN that is configured to take the real and imaginary parts of the button impedances ($\text{Re}(Z_b^{F1})$, Im($Z_b^{F1}$), (Re($Z_b^{F2}$), Im($Z_b^{F2}$)) at both frequencies F1 and F2 and $Z_{90}^{F2}$ as inputs to predict and output the mud impedance angle $\varphi_m^{F2}$ at the frequency F2.

ANN3 is an ANN that is configured to take the real and imaginary parts of the button impedances (Re($Z_b^{F1}$), Im($Z_b^{F1}$)), (Re($Z_b^{F2}$), Im($Z_b^{F2}$)) at both frequencies F1 and F2 as inputs to predict and output the ratio S/$\varepsilon_m^{F1}$.

ANN4 is an ANN that is configured to take real and imaginary parts of the button impedances (Re($Z_b^{F1}$), Im($Z_b^{F1}$)), (Re($Z_b^{F2}$), Im($Z_b^{F2}$)) at both frequencies F1 and F2 as inputs to predict and output the ratio S/$\varepsilon_m^{F2}$.

ANN5 is an ANN that is configured to take the real and imaginary parts of the button impedance (Re($Z_b^{F2}$), Im($Z_b^{F2}$)) at frequency F2 as well as $Z_{90}^{F2}$ to predict and output the mud dielectric permittivity $\varepsilon_m^{F2}$.

CALC6 is a computational module that is configured to utilize the outputs of ANN3, ANN4 and ANN5 to calculate $\varepsilon_m^{F1}$. Specifically, $\varepsilon_m^{F2}$ as output by ANN5 times S/$\varepsilon_m^{F2}$ as output by ANN4 can provide S, and the resultant S divided by the ratio of $\varepsilon_m^{F1}$ as output by ANN3 can provide $\varepsilon_m^{F1}$.

ANN7 is an ANN that is configured to take the real and imaginary parts of the button impedances (Re($Z_b^{F1}$), Im($Z_b^{F1}$)), (Re($Z_b^{F2}$), Im($Z_b^{F2}$)) at both frequencies F1 and F2, $\varphi_m^{F1}$ from ANN1, $\varepsilon_m^{F1}$ from CALC6, $\varphi_m^{F2}$ from ANN2, and $\varepsilon_m^{F2}$ from ANN5 as inputs to predict and output the standoff S and formation resistivity $R_t$.

ANN8 is an ANN that is configured to take the real and imaginary parts of the button impedance (Re($Z_b^{F1}$), Im($Z_b^{F1}$)) at frequency F1, $\varphi_m^{F1}$ from ANN1, $\varepsilon_m^{F1}$ from CALC6, S and $R_t$ from ANN7 and $Z_{90}^{F1}$ as inputs to predict and output the formation dielectric permittivity, $\varepsilon_f^{F2}$, at frequency F1.

ANN9 is an ANN that is configured to take the real and imaginary parts of the button impedance (Re($Z_b^{F2}$), Im($Z_b^{F2}$)) at frequency F2, $\varepsilon_m^{F2}$ from ANN2, $\varepsilon_m^{F2}$ from ANN5, S and $R_t$ from ANN7 and $Z_{90}^{F2}$ as inputs to predict and output the formation dielectric permittivity, $\varepsilon_f^{F2}$, at frequency F2.

The button measurements can be sensitive to mud properties in the regions with low formation resistivity. The inversion-based workflows can exploit this fact and perform inversion for the mud properties in a small log section, approximately 10 ft, where the approximate formation resistivity $Z_{90}^{F1}$ and $Z_{90}^{F2}$ are low and accurate. A similar approach can be employed for prediction of mud properties via the system of cascaded feed forward ANNs. Specifically, ANN1, ANN2, ANN3, ANN4, ANN5 and CALC 6 can be used in low resistivity regions. Once, the low resistivity region is identified, the button measurements at the two frequencies F1 and F2 are processed and the results fed as inputs to the trained system of cascaded feedforward ANNs to predict the mud angle properties. The button measurements can include values in a very large dynamic range. In this case, the dynamic range can be reduced by applying a log 10 transformation to the input data. The inputs can also be normalized before being fed into the trained system of cascaded feedforward ANNs to ensure robust performance.

Note that ANN1 and ANN2 can employ multilayered fully connected ANN architectures which are trained separately for the two respective frequencies F1 and F2. ANN1 and ANN2 can also employ artificial neurons operated on rectified-linear unit (ReLU) activation for introducing non-linearity. The ReLU function can be defined as f(x)=max(x, 0).

For ANN3 and ANN4, the inputs can be log 10 transformed to reduce the dynamic range and then normalized before being fed into the ANNs. ANN3 and ANN4 can also employ multilayered feedforward ANN architectures with ReLU activation functions.

ANN5, ANN7, ANN8 and ANN 9 can also employ multilayered feedforward ANN architectures with ReLU activation functions.

Figure 5B:
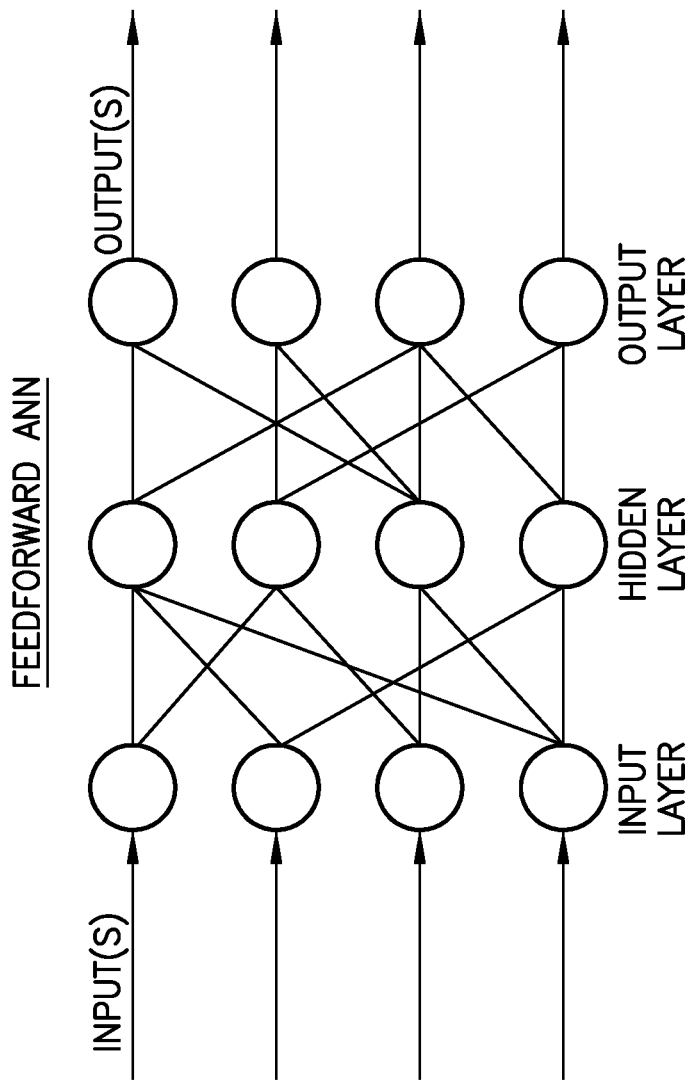
FIG. 5B is a diagram illustrating a feedforward ANN.

FIG. 5B depicts a feedforward neural network architecture, which can be used to embody the ANNs of the system of cascaded ANNs as described herein. In the feedforward neural network architecture, the connections between the artificial neurons do not form a cycle. The information moves in only one direction, forward, from the input layer to the hidden layer(s), and to the output layer. There are no cycle or loops in the network. In this case, the artificial neurons of a given hidden layer can connect to artificial neurons of the immediately preceding and immediately following layers.

The separate and distinct ANNs of the system can be trained independently from one another. Synthetic data, previously-inverted field data, or combinations thereof can be used as ground truth observations for training the ANNs of the system. For example, ANN1 can be trained by extracting the real and imaginary parts of synthetic or field-measured button impedance (Re($Z_b^{F1}$), Im($Z_b^{F1}$)) at the frequency F1 as well the impedance component $Z_{90}^{F2}$ for the synthetic or field-measured button impedance at the frequency F2. This data is supplied as inputs to ANN1, which predicts and outputs a mud impedance angle $\varphi_m^{F1}$ at the frequency F1, which is compared to a ground truth mud impedance angle $\varphi_m^{F1}$ at the frequency F1 which is known from the synthetic measurements or field data. The difference between the predicted mud impedance angle $\varphi_m^{F1}$ and ground truth mud impedance angle $\varphi_m^{F1}$ can be used to train or update ANN1, for example by updating the weights (and possibly thresholds) of ANN1 to improve the accuracy of the mud impedance angle $\varphi_m^{F1}$ predicted by ANN1. This training process can be repeated multiple times for several synthetic or field-measured button impedance values in order to train ANN1. Similar operations can be performed to train the other ANNs of the system. Furthermore, the training can be adapted to target specific scenarios and generate more robust interpretation for a formation and parameter ranges.

Figure 6:
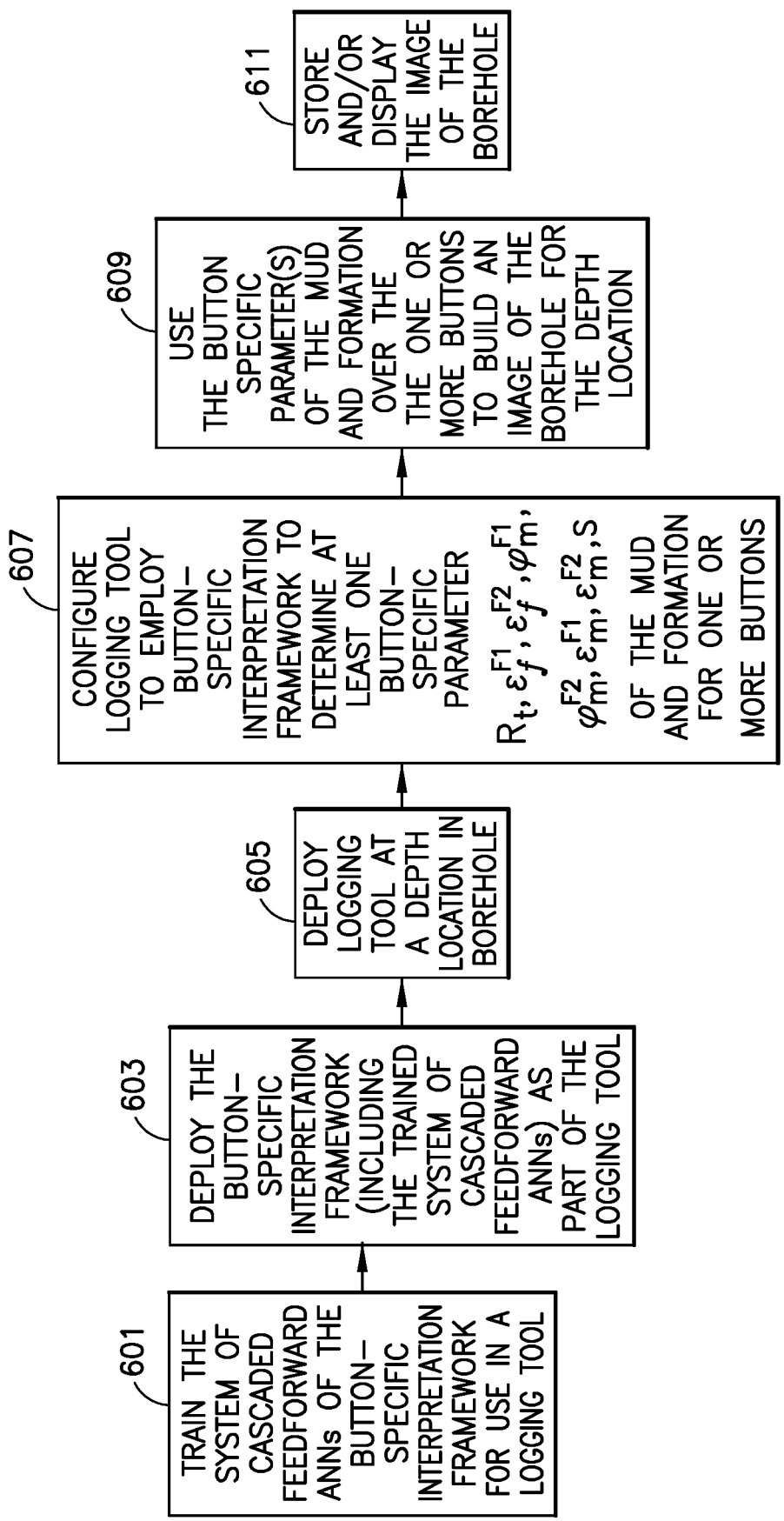
FIG. 6 is a flow chart of a workflow that employs the interpretation framework of FIG. 4 for a well logging application.

FIG. 6 is a flow chart of an interpretation workflow that utilizes the button-specific interpretation framework of FIG. 4 for well-logging applications. The operations begin in block 601 where the ANNs of the system are trained for use in a logging tool, such as the logging tool 10 of FIG. 2.

In block 603, the button-specific interpretation framework (including the trained system of cascaded Feedforward ANNs) are deployed as part of the logging tool. For example, the button-specific interpretation framework (including the trained system of cascaded feedforward ANNs) can be implemented on a processor-based system or module that is housed as part of the logging tool.

In block 605, the logging tool (with the button-specific interpretation framework) is deployed at a depth location in a borehole.

In block 607, the logging tool can be configured to employ the button-specific interpretation framework to predict and output button-specific parameters of the mud and formation interval traversed by the borehole for one or more buttons. For example, the button-specific parameters can include one or more of the eight parameters $R_t$, $\varepsilon_f^{F1}$, $\varepsilon_f^{F2}$, $\varphi_m^{F1}$, $\varphi_m^{F2}$, $\varepsilon_m^{F1}$, $\varepsilon_m^{F2}$, S for a button.

In block 609, the button-specific parameter(s) of the mud and formation interval traversed by the borehole for one or more buttons is used to build an image of the borehole for the depth location of the tool. For example, the outputs of the button-specific interpretation framework can be configured to predict and output mud and formation parameters for the buttons at varying azimuthal coordinates and possibly varying depth coordinates in the borehole. Such parameters can be integrated into one or more images of the borehole or other log. Examples of such images are shown in FIGS. 7B, 8B and 9B below.

In block 611, the image(s) produced in block 609 can be stored in electronic form and/or displayed or otherwise presented to a user for formation analysis as desired.

In alternate embodiments, if field measurement data is available (such as from inversion-based processing), the field measurement data can be used to train new and separate ANNs that can predict certain formation unknowns or standoff.

FIG. 7A is an image of formation resistivity for a borehole interval as produced by inversion processing, while FIG. 7B is an image of formation resistivity for the same borehole interval as produced by the ANN-based button-specific interpretation framework described herein. FIG. 7C shows the scale of the resistivity values for the images of FIGS. 7A and 7B. These images show that the ANN-based button-specific interpretation framework described herein produces similar results to those produced by inversion processing.

FIG. 8A is an image of tool standoff for a borehole interval as produced by inversion processing, while FIG. 8B is an image of tool standoff for the same borehole interval as produced by the ANN-based button-specific interpretation framework described herein. FIG. 8C shows the scale of the standoff values for the images of FIGS. 8A and 8B. These images show that the ANN-based button-specific interpretation framework described herein produces similar results to those produced by inversion processing.

FIG. 9A is an image of formation permittivity for a borehole interval as produced by inversion processing, while FIG. 9B is an image of formation permittivity for the same borehole interval as produced by the ANN-based button-specific interpretation framework described herein. FIG. 9C shows the scale of the formation permittivity values for the images of FIGS. 9A and 9B. These images show that the ANN-based button-specific interpretation framework described herein produces similar results to those produced by inversion processing.

Figure 10:
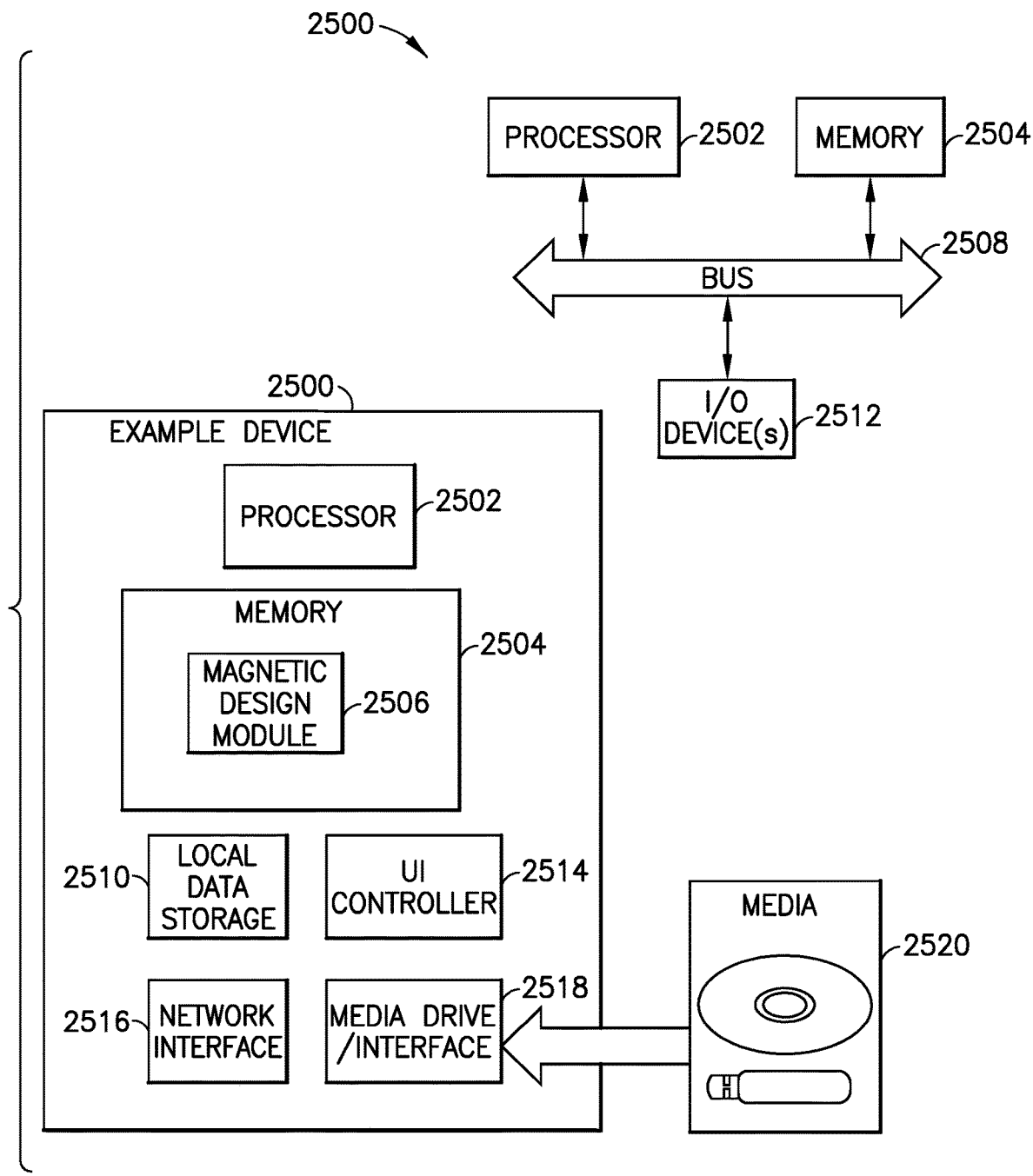
FIG. 10 is a block diagram of a computer processing system that can incorporate aspects of the subject disclosure.

FIG. 10 illustrates an example device 2500, with a processor 2502 and memory 2504 that can be configured to implement various embodiments of the ANN-based button-specific interpretation framework as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500 and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of present disclosure may be described herein in the general context of software or program modules, or the techniques and modules may be implemented in pure computing hardware. Software generally includes routines, programs, objects, components, data structures, and so forth that perform tasks or implement abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of predicting electromagnetic properties of drilling mud and a formation, the method comprising:
    configuring a logging tool to i) apply an alternating voltage of multiple frequencies to a sensor electrode that injects current into a measurement zone disposed adjacent the sensor electrode, wherein the measurement zone includes the drilling mud and the formation, and ii) measure values of the current injected into the measurement zone at the multiple frequencies;
    processing the measured values of the current at the multiple frequencies to determine complex impedances for the sensor electrode at the multiple frequencies;
    generating input data based on the complex impedances for the sensor electrode at the multiple frequencies;
    supplying the input data to a system of artificial neural networks (ANNs) that is configured to predict and output the electromagnetic properties of the drilling mud and the formation within the measurement zone based on the input data, wherein the system of ANNs employs a cascaded architecture of multiple ANNs; and
    generating a borehole image over varying azimuth and depth using the electromagnetic properties.

2. The method according to claim 1, wherein:
the electromagnetic properties predicted and output by the system of ANNs include a formation resistivity as well as formation permittivities for the multiple frequencies.

3. The method according to claim 1, wherein:
the electromagnetic properties predicted and output by the system of ANNs include mud permittivities for the multiple frequencies.

4. The method according to claim 1, wherein:
the system of ANNs is further configured to predict and output a tool standoff for the sensor electrode based on the input data.

5. The method according to claim 4, further comprising:
using the tool standoff predicted and output by the system of ANNs to construct the borehole image over varying azimuth and depth.

6. The method according to claim 5, further comprising:
repeating or replicating operations of the method for multiple sensor electrodes, wherein the borehole image is constructed by combining the electromagnetic properties or the tool standoff predicted and output by the system of artificial neural networks for the multiple sensor electrodes.

7. The method according to claim 1, wherein:
the system of ANNs employs a cascaded architecture of multiple feedforward ANNs.

8. The method according to claim 7, wherein:
the cascaded architecture of multiple feedforward ANNs employs i) a first plurality of feedforward ANNs that predict and output mud impedance angles for the multiple frequencies, and ii) a second plurality of feedforward ANNs that predict and output formation permittivities for the multiple frequencies based on outputs of the first plurality of feedforward ANNs.

9. The method according to claim 8, wherein:
the cascaded architecture of multiple feedforward ANNs further employs i) a third plurality of feedforward ANNs that predict and output ratios of tool standoff and mud permittivity for the multiple frequencies as well as mud permittivity for one frequency of the multiple frequencies, and ii) a computational module that calculates mud permittivity for another frequency of the multiple frequencies based on outputs of the third plurality of feedforward ANNs.

10. The method according to claim 9, wherein:
the cascaded architecture of multiple feedforward ANNs further employs a fourth feedforward ANN that predicts and outputs formation resistivity and the tool standoff based on the outputs of the first plurality of feedforward ANNs, the outputs of the third plurality of feedforward ANNs and the computational module.

11. The method according to claim 10, wherein:
the second plurality of feedforward ANNs also uses the formation resistivity and the tool standoff output by the fourth feedforward ANN as input in order to predict and output the formation permittivities for the multiple frequencies.

12. The method according to claim 1, wherein:
the ANNs of the system of ANNs are trained using synthetic or previously-inverted field data.

13. The method according to claim 1, wherein:
the ANNs of the system of ANNs are trained independently from one another.

14. The method according to claim 1, further comprising:
storing in electronic form or outputting the electromagnetic properties predicted and output by the system of ANNs.

15. The method according to claim 1, wherein:
the drilling mud comprises an oil-based mud.

16. A system for predicting electromagnetic properties of drilling mud and a formation, the system comprising at least one processor that, when executing program instructions stored in memory, is configured to:
obtain measurements of current injected into a measurement zone adjacent a sensor electrode at multiple frequencies, wherein the measurement zone includes the drilling mud and the formation;
process the measurements of the current at the multiple frequencies to determine complex impedances for the sensor electrode at the multiple frequencies;
generate input data based on the complex impedances for the sensor electrode at the multiple frequencies; and
supply the input data to a system of artificial neural networks (ANNs) that is configured to predict and output electromagnetic properties of the drilling mud and the formation within the measurement zone based on the input data, wherein the system of ANNs employs a cascaded architecture of multiple ANNs and generate a borehole image over varying azimuth and depth using the electromagnetic properties.

17. The system according to claim 16, wherein: the at least one processor is further configured to use a tool standoff predicted and output by the system of ANNs to construct the borehole image over varying azimuth and depth" to provide appropriate antecedence basis.

18. The system according to claim 17, wherein:
the at least one processor is further configured to repeat or replicate the program instructions for multiple sensor electrodes, wherein the borehole image is constructed by combining the electromagnetic properties or the tool standoff predicted and output by the system of artificial neural networks for the multiple sensor electrodes.

19. The system according to claim 16, wherein:
the measurements of the current at the multiple frequencies are performed by a downhole logging tool that applies an alternating voltage to the sensor electrode to inject the current into the measurement zone adjacent the sensor electrode.

20. The system according to claim 19, wherein:
the downhole logging tool is one of a wireline logging tool or a measurement-while-drilling logging tool.

21. The system according to claim 16, wherein:
the drilling mud comprises an oil-based mud.

* * * * *